(12) United States Patent
Granzow et al.

(10) Patent No.: US 6,376,224 B1
(45) Date of Patent: Apr. 23, 2002

(54) PHARMACEUTICAL COMPOSITIONS FOR ELIMINATING MEMBRANE-MEDIATED CELL RESISTANCE

(75) Inventors: Christoph Granzow; Herwig Ponstingl; Irmgard Hefft; Marijana Kopun-Granzow; Gabriele Gros, all of Heidelberg; Michael Stöhr, Neckargerach, all of (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/381,651

(22) PCT Filed: Mar. 18, 1998

(86) PCT No.: PCT/DE98/00814

§ 371 Date: Mar. 3, 2000

§ 102(e) Date: Mar. 3, 2000

(87) PCT Pub. No.: WO98/41236

PCT Pub. Date: Sep. 24, 1998

(30) Foreign Application Priority Data

Mar. 17, 1997 (DE) .......................................... 197 11 503

(51) Int. Cl.[7] .......................... C12N 13/00; A61K 38/00
(52) U.S. Cl. ...................... 435/173.1; 514/11; 514/51; 514/523
(58) Field of Search ............................ 514/11, 523, 51; 435/173.1

(56) References Cited

FOREIGN PATENT DOCUMENTS

EP          3635930 A1      4/1988

OTHER PUBLICATIONS

Nasioulas et al, Eur. J. Biochem., vol. 28, #1, pp. 69–74 (abstract), Aug. 1990.*
Nasioulas et al, Cancer Res., vol. 15, #2, pp. 403–8 (abstract), Jan. 1990.*
Jachez et al, J. Natl. Cancer Inst., vol. 17, #6, pp. 478–83 (abstract), Mar. 1993.*
Aguero, et al. "Verapamil Increases Rhodamine 123 Laser Phototherapy of Drug–Resistant Human Sarcoma Cells," Journal of Clinical Laser Medicine & Surgery, vol. 12, No. 4 (1994), pp. 193–198.
Maziere, et al. "Potentialisation de l'effet Photocytotoxique du Photofrin II: actions synergiques du verapamil et de lovastatine," Bull. Acad. Natle. Med., vol. 178, No. 6 (1994), pp. 1177–1189.
Mote, et al. "Paclitaxel Sensitizes Multidrug Resistant Cells to Radiation," Anti–Cancer Drugs, vol. 7 (1996), pp. 182–188.
Chorvath, et al. "Letter to the Editor: Non–immunosuppressive Cyclosporine Derivative PSC 833 Abolishes Resistance of Human Multrdrug–resistant Ovarian Carcinoma Cells in Vitro to Paclitaxel and Paclitaxel–induced Radiosensitization," Int. J. Cancer, vol. 72 (1997), pp. 916–917.
Kellen "The Reversal of Multidrug Resistance in Cancer (Review)," Anticancer Research, vol. 13 (1993), pp. 959–961.

* cited by examiner

*Primary Examiner*—James H. Reamer
(74) *Attorney, Agent, or Firm*—Steven J. Hultquist; Marianne Fuierer

(57) ABSTRACT

The invention relates to a pharmaceutical composition containing an inhibitor for diaphragm pumps and a photoaffinity-marked chemotherapeutic agent. Said composition is suitable for eliminating membrane-mediated cell resistance, especially membrane-mediated multi-chemoresistance of tumor cells.

12 Claims, No Drawings

PHARMACEUTICAL COMPOSITIONS FOR ELIMINATING MEMBRANE-MEDIATED CELL RESISTANCE

The present invention relates to a pharmaceutical composition for eliminating the membrane-mediated resistance of cells, particularly the membrane-mediated multi-chemoresistance of tumor cells, and a process for this by using this composition.

When membrane-mediated resistance of prokaryotic and eukaryotic cells, particularly cytostatic agent-resistance of tumor cells, comes about, membrane-bound transport mechanisms often play a key role. An example of such a membrane-bound transport mechanism is based on the activity of P-glycoprotein. The P-glycoprotein is a transmembrane protein having the function of a cellular outward transport of substrates. Substrates of this membrane-bound transport mechanism are many clinically significant cytostatic agents. This means that the cytostatic agents are transported out of (eliminated from) the cells by this membrane-bound transport mechanism. Such cells are thus resistant to cytostatic agents. Inhibitors of this membrane-bound transport mechanism have been used in tumor patients so far to reduce the outward transport and thus the resistance. However, such inhibitors must be administered in high concentration over a very long period of time which often covers up to several days. Therefore, side-effects occur which greatly strain the organism. In addition, only a temporary reduction, but no elimination of resistance, is achieved by the administration of these inhibitors.

Thus, it is the object of the present invention to provide a pharmaceutical composition by which the membrane-mediated resistance of cells, particularly tumor cells, is terminated rapidly and completely without side-effects worth mentioning.

According to the invention this is achieved by the subject matters defined in the claims.

Therefore, the subject matter of the present invention relates to a pharmaceutical composition containing an inhibitor for membrane pumps and a photoaffinity-labeled chemotherapeutic agent.

The expression "inhibitor for membrane pumps" comprises any kinds of compounds which inhibit (block) membrane-bound transport mechanisms, particularly transport mechanisms for the outward transport, e.g. a P-glycoprotein-mediated outward transport. A person skilled in the art knows a plurality of such inhibitors. Particularly favorable inhibitors are verapamil and its derivatives as well as cyclosporine A and its derivatives, e.g. PSC 833. Several different such inhibitors can also be present in the pharmaceutical composition according to the invention.

The expression "photoaffinity-labeled chemotherapeutic agent" comprises compounds of any kind which have a chemotherapeutic agent and a photoaffinity marking. Chemotherapeutic agents are compounds suitable for treating infectious diseases caused by bacteria, viruses, protozoa, fungi and worms and cancerous diseases, cytostatic agents being particularly preferred. Photoaffinity markings are compounds which by irradiation using light can be converted into a form reacting with cellular components thereby forming covalent bonds. A person skilled in the art knows a plurality of such photoaffinity markings. It has proved favorable for the photoaffinity marking to comprise an azide grouping, since under physiological conditions it can be converted especially well into a form which binds to cellular components. The photoaffinity-labeled chemotherapeutic agent napavin is particularly preferred. It is derived from vinblastine where an acetyl group is replaced by an azide-comprising group. Several different photoaffinity-labeled chemotherapeutic agents can be present in the pharmaceutical composition according to the invention.

The composition according to the invention has a molar ratio of inhibitor:photoactivity-labeled chemotherapeutic agent of 1:10 to 10:1, preferably 5:1 to 3:1.

A composition according to the invention can contain common auxiliary agents. The auxiliary agents used can be the conventional ones, such as carriers, binders, blasting agents, lubricants, solvents, solution aids, release accelerators, release retarders, emulsifiers, stabilizers, coloring agents or taste corrigents. The pharmaceutical composition according to the invention can also be present in the form of a sterile physiological common-salt solution, i.e. inhibitor and photoaffinity-labeled chemotherapeutic agent are dissolved in a sterile physiological common-salt solution. The dissolution is carried out by optionally adding a solution aid such as alcohol, e.g. ethanol and benzyl alcohol.

The amount of inhibitor and photoaffinity-labeled chemotherapeutic agent in the pharmaceutical composition can be 0.1 to 10, particularly about 1 mg per 1000 g of composition.

The composition according to the invention can be applied as usual, e.g. locally, topically or systemically. It is useful for the composition according to the invention to be applied in intraarterially regional fashion, i.e. to certain regions of the body via supplying arteries, for a period of 5 to 30 minutes, more preferably of about 10 minutes. Immediately afterwards, exposure is carried out directly, e.g. in the case of superficial cells, or endoscopically. The period of exposure is 1 to 5, particularly about 1 minute. In this connection, laser light or incoherent light can be used as light source, optionally by using filters. The wavelength and the intensity of the light are chosen in this case as a function of the employed photoaffinity marking.

The application can be 1 to 5, particularly 1 to 3, and most particularly 1, times daily. The application can be carried out on several successive days.

The subject matter of the present invention also relates to a method of eliminating the membrane-mediated resistance of cells, comprising the steps of:
 a) influence of a composition according to the invention on cells, and
 b) exposure of the cells.

The cells are cells having membrane-mediated resistance, particularly membrane-mediated multi-chemoresistance. They can be present in a common cell culture. The cells are preferably tumor cells. The influence of the composition according to the invention lasts several minutes, preferably 5 to 30, and more preferably about 10 minutes. The exposure is carried out as described above. The exposure period is few minutes, preferably 1 to 5 and more preferably about 1 minute. Following exposure, the cells can be cultured. The cell growth is measured after the culturing (e.g. after three days) and the 50% inhibitory concentration is determined graphically as usual. The mechanisms underlying membrane-mediated resistance can be studied by means of this method.

The present invention distinguishes itself in that the membrane-mediated resistance of cells, particularly tumor cells, is eliminated by interaction of an inhibitor for membrane pumps and a photoactivity-labeled chemotherapeutic agent in combination with an exposure. In this connection, elimination takes place rapidly. Furthermore, only short exposure times and small substance amounts are necessary for the application of the pharmaceutical composition according to the invention. Thus, the composition according to the invention has little side-effects. It has no genotoxic (gene-damaging) effect. The exposure is carried out only for a short period of time, so that the cells or tissue do not heat in undesired fashion. Furthermore, the growth of resistant tumor cells, even of those having a very distinct membrane-mediated multi-chemoresistance, and of non-resistant tumor cells is prevented when the composition according to the invention is administered.

Together with the method of resistance suppression according to the invention the composition according to the invention is perfectly suited to trigger cell death programs (apoptosis). Therefore, it is suitable for treating diseases where a membrane-mediated resistance, particularly a membrane-mediated multi-chemoresistance, may occur as in the case of infectious diseases and tumoral diseases, particularly tumoral diseases of skin, urothelial and rectal tissues, that of the upper aerodigestive tract including the esophagus and that within the region of pleura and peritoneum. The expression 'tumoral diseases' also includes primary tumors and metastases.

The following example explains the invention.

EXAMPLE

Elimination of P-glycoprotein-mediated Multi- chemoresistance of Mouse Ascites Cells and Human Carcinoma Cells.

Chemosensitive mouse ascites cells (strain HD34K) were compared with their variant (strain SR) which distinuishes itself by P-glycoprotein-mediated multi-chemoresistance. The chemoresistance of the SR cells developed spontaneously. The mouse ascites cells were suspended in fresh cell culture medium before the experiment started.

In addition, chemosensitive KB cells (human carcinoma cells) were compared with their chemoresistant KBC5-8 variant. The multi-chemoresistance of the latter is also P-glycoprotein-mediated and was induced experimentally by colchicine addition to the cell culture medium. Before the experiment started, the human carcinoma cells were typsinized and suspended in fresh cell culture medium.

All of the experiments were carried out under flavin-protecting test conditions (Granzow et al., Cancer Res. 55, 4837–4843, (1995)). Freshly prepared cell suspensions were previously incubated at 36.5° C. for 15 minutes. Then, the cells were incubated with graded concentrations of vinblastin and napavin (photoactivity-labeled cytostatic agent). The incubation was carried out either in the absence of verapamil (inhibitor for P-glycoprotein) or, in the case of vinblastin, with 1 $\mu$M verapamil and, in the case of napavin, with 1 or 2 $\mu$M verapamil, respectively. The mouse ascites cells were incubated with these pharmacetuical agents for five minutes. The human tumor cells were incubated for ten minutes. Then, the cell suspensions were transferred by pipetting into plastic dishes or trays and exposed using an argon laser (457.8 nm, 48 mW/cm$^2$) at room temperature for 1 minute. Thereafter, the cells were washed with fresh cell culture medium twice and cultured in 24-well multidishes or multitrays for three days. At the end of the experiment, cell growth was measured and the 50% inhibitory concentration of the cytostatic agents vinblastin and napavin was determined graphically as usual. The results are shown in the below table.

TABLE

| | 50% micromolar inhibitory concentrations | | | | |
|---|---|---|---|---|---|
| Cell strain | VLB | VLB + 1 $\mu$M VPM | NAP | NAP + 1 $\mu$M VPM | NAP + 2 $\mu$M VPM |
| KB (w. t.) | 0.16 +/− 0.01 | 0.18 +/− 0.01 | 0.16 | 0.15 | n.d. |
| KBC5-8 (mdr) | 27 +/− 1 | 28 | 3.8 +/− 0.9 | 1.0 +/− 0.1 | 0.35 +/− 0.15 |
| HD34K (w. t.) | 0.66 | 0.75 | 0.43 +/− 0.05 | 0.33 +/− 0.01 | n.d. |
| SR (mdr) | 7 | 9 | 4.75 +/− 0.5 | 0.9 +/− 0.15 | 0.6 |

Abbreviations: w.t.: chemosensitive wild-type cells; mdr: multi-chemoresistant variants; n.d.: not determined; VLB: vinblastin; VPM: verapamil; NAP: napavin.

As follows from the table, the concentrations of vinblastin and napavin required for 50% growth suppression was between 0.1 and 0.2 $\mu$M in the case of the chemosensitive human KB cells. Verapamil had no influence on it. In the case of the multi-resistant variant KBC5-8 about 150 times the vinblastin concentration was required for the same effect. This corresponds to an excessive resistance degree. Verapamil had no influence on it. In the case of napavin 23 times of the concentration required for KB cells was necessary without verapamil. With verapamil additionally in the batch, it was still 6 times as much, and with 2 $\mu$M verapamil it was only twice as much. In the light of the variation ranges, there is no longer a significant difference with respect to the wild-type, i.e. resistance has been eliminated.

In the case of the chemosensitive HD34K ascites cells of mice, the 50% inhibitory concentration of vinblastin was 0.66 $\mu$M without verapamil, in the presence of 1 $\mu$M verapamil it was insignificantly higher. With a napavin addition, about 0.4 $\mu$M were required for the same effect, and slightly less was required with an addition of 1 $\mu$M verapamil. In the case of the multi-resistant variant SR, 50% growth inhibition occurred with vinblastin in the case of about 10 times the wild-type concentration. This corresponds to a mean resistance level as observed with human, multi-resistant tumors. In connection with napavin, this ratio is also 10 to 1 in the absence of verapamil. However, with 1 $\mu$M verapamil in the batch, the measured inhibitory concentrations no longer differ significantly, with 2 $\mu$M verapamil they become identical.

Summarizing it must be stated that in the case of joint administration of napavin and verapamil and subsequent exposure multi-chemoresistant cells become as chemosensitive as their parental wild-type cells, i.e. complete elimination of resistance can be observed.

What is claimed is:

1. A pharmaceutical composition comprising an inhibitor for membrane pumps and a photoaffinity-labeled chemotherapeutic agent.

2. The pharmaceutical composition according to claim 1, wherein the inhibitor for membrane pumps comprises an inhibitor for membrane pumps for outward transport.

3. The pharmaceutical composition according to claim 2, wherein the inhibitor comprises an inhibitor of the transport mediated by P-glycoprotein.

4. The pharmaceutical composition according to claim 3, wherein the inhibitor comprises an agent selected from the group consisting of verapamil, cyclosporine A and derivatives thereof.

5. The pharmaceutical composition according to claim 1, wherein the chemotherapeutic agent comprises a cytostatic agent.

6. The pharmaceutical composition according to claim 1, wherein the photoaffinity-labeled chemotherapeutic agent comprises an azide.

7. A pharmaceutical composition comprising an inhibitor for membrane pumps and a photoaffinity-labeled chemotherapeutic agent, wherein the photoaffinity-labeled chemotherapeutic agent comprises napavin.

8. A process for eliminating the membrane-mediated resistance of cells, comprising the steps of:
   a) influence of a pharmaceutical composition according to claim 1 on cells, and
   b) exposure of the cells.

9. The process according to claim 8, wherein the exposure is carried out by means of a laser or coherent light.

10. The process according to claim 8, characterized in that the cells are tumor cells.

11. Use of the pharmaceutical composition according to claim 1 for eliminating membrane-mediated resistance of cells.

12. Use of the pharmaceutical composition according to claim 1 for triggering apoptosis in tumor cells.

* * * * *